United States Patent
Van Krieken et al.

(10) Patent No.: US 10,626,069 B2
(45) Date of Patent: Apr. 21, 2020

(54) METHOD FOR PREPARING METHYL LACTATE

(71) Applicant: PURAC BIOCHEM BV, Gorinchem (NL)

(72) Inventors: Jan Van Krieken, Gorinchem (NL); André Banier De Haan, Gorinchem (NL); Jan Van Breugel, Gorinchem (NL)

(73) Assignee: PURAC BIOCHEM B.V., Gorinchem (NL)

( * ) Notice: Subject to any disclaimer, the term of this patent is extended or adjusted under 35 U.S.C. 154(b) by 318 days.

(21) Appl. No.: 14/767,004

(22) PCT Filed: Feb. 13, 2014

(86) PCT No.: PCT/EP2014/052815
§ 371 (c)(1),
(2) Date: Aug. 11, 2015

(87) PCT Pub. No.: WO2014/125020
PCT Pub. Date: Aug. 21, 2014

(65) Prior Publication Data
US 2015/0376107 A1    Dec. 31, 2015

Related U.S. Application Data

(60) Provisional application No. 61/764,628, filed on Feb. 14, 2013.

(30) Foreign Application Priority Data

Feb. 14, 2013    (EP) .................................... 13155241

(51) Int. Cl.
| | | |
|---|---|---|
| *C07C 29/09* | (2006.01) | |
| *C12P 7/62* | (2006.01) | |
| *C07C 67/38* | (2006.01) | |
| *C07C 67/08* | (2006.01) | |
| *C07C 29/149* | (2006.01) | |

(52) U.S. Cl.
CPC ............ *C07C 29/095* (2013.01); *C07C 67/08* (2013.01); *C07C 67/38* (2013.01); *C12P 7/62* (2013.01); *C07C 29/149* (2013.01)

(58) Field of Classification Search
CPC ....... C07C 29/095; C07C 67/38; C07C 67/08; C07C 29/149; C12P 7/62
See application file for complete search history.

(56) References Cited

U.S. PATENT DOCUMENTS 2,417,748 A * 3/1947 Hagemeyer, Jr. ...... C07C 67/327
558/311
2014/0335581 A1* 11/2014 De Haan ................ B01D 11/04
435/139

FOREIGN PATENT DOCUMENTS

| DE | 232 818 C | 3/1911 |
|---|---|---|
| DE | 20 50 678 A1 | 4/1972 |
| GB | 1 282 926 A | 7/1972 |
| JP | 2004-315411 A | 11/2004 |
| JP | 2006-232689 A | 9/2006 |
| KR | 2011-0099119 A | 9/2011 |
| WO | 00/017378 A2 | 3/2000 |
| WO | WO 2005123647 A1 * | 12/2005 ............. C07C 51/02 |

OTHER PUBLICATIONS

Anonymous. Polarity Index (2016) downloaded from http://www.macro.lsu.edu/howto/solvents/Polarity%20index.htm on Jul. 29, 2016.*
May 13, 2014 Search Report issued in International Patent Application No. PCT/EP2014/052815.
May 13, 2014 Written Opinion issued in International Patent Application No. PCT/EP2014/052815.
Poma et al; "The action of neutral salts on the constants of chemical equilibrium III;" XP002701098; 1915; Proceedings of the National Academy of Lincei, Class of Physics, Mathematics and Natural Reports; vol. 24; No. II; pp. 43-51.
Poma et al; "The action of neutral salts on the constants of chemical equilibrium;" XP002701099; 1915; Proceedings of the National Academy of Lincei, Class of Physics, Mathematics and Natural Reports; vol. 24; No. I; pp. 747-754.
Poma et al; "The action of neutral salts on the constants of chemical equilibrium II;" XP002701100; 1915; Proceedings of the National Academy of Lincei, Class of Physics, Mathematics and Natural Reports; vol. 24; No. II; pp. 979-985.
Nov. 14, 2016 Office Action issued in Japanese Patent Application No. 2015-557424.

(Continued)

*Primary Examiner* — Juliet C Switzer
*Assistant Examiner* — Paul C Martin
(74) *Attorney, Agent, or Firm* — Oliff PLC

(57) ABSTRACT

The invention pertains to a process for preparing methyl lactate including the steps of: bringing an aqueous liquid comprising lactic acid, methanol, and at least 5 wt. % of a dissolved chloride salt selected from magnesium chloride, calcium chloride, and zinc chloride to reaction conditions, thereby obtaining methyl lactate, wherein an extractant is provided to the reaction mixture before, during, and/or after formation of methyl lactate; subjecting the reaction mixture to a liquid-liquid separation step wherein an organic phase comprising methyl lactate and extractant is separated from an aqueous phase comprising dissolved chloride salt. The extractant preferably includes one or more compounds selected from C5+ ketones and C3-C10 ethers, in particular C5-C8 ketones, more in particular methyl isobutyl ketone. It has been found that the process according to the invention makes it possible to manufacture methyl lactate efficiently and in high yield.

20 Claims, 4 Drawing Sheets

(56) References Cited

OTHER PUBLICATIONS

Figure 1:
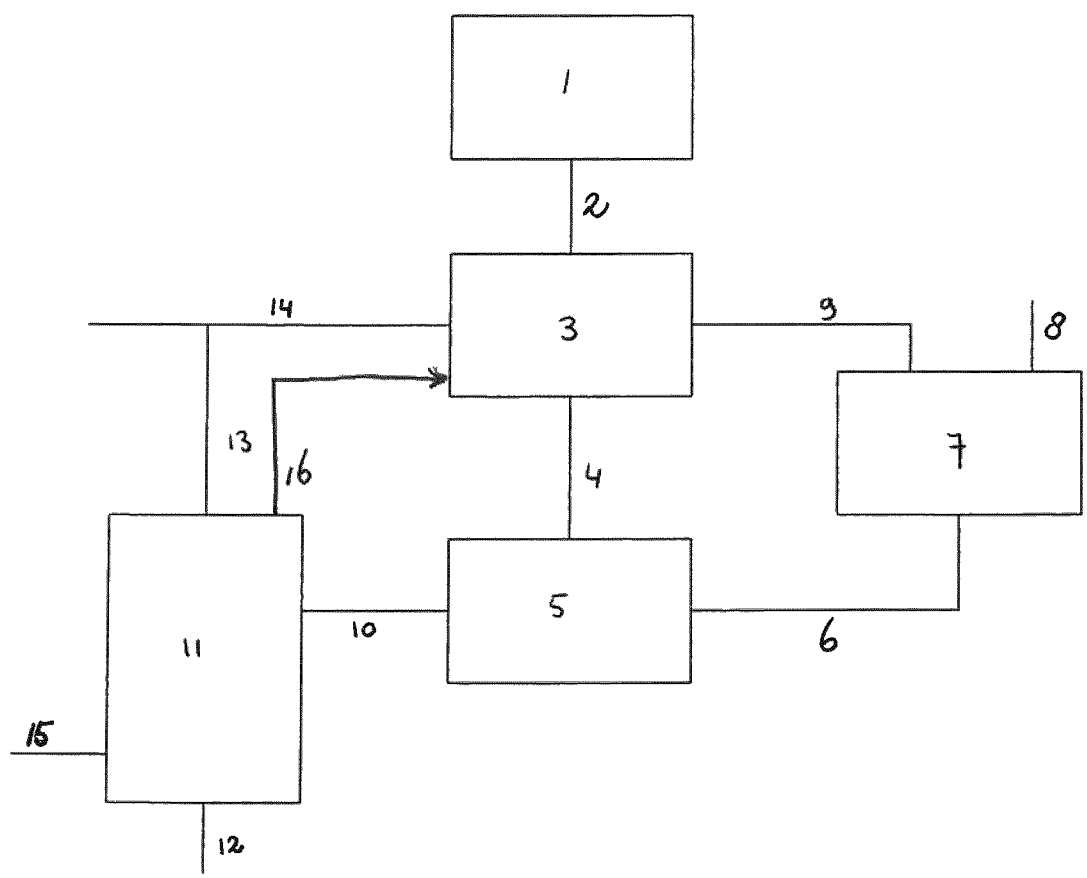

Feb. 20, 2017 Office Action issued in Korean Patent Application No. 10-2015-7024756.
Sep. 12, 2017 Office Action issued in Chinese Application No. 201480008221.1.

* cited by examiner

METHOD FOR PREPARING METHYL LACTATE

The present invention is directed to a method for methyl lactate, and to a method for manufacturing methyl acrylate.

Methyl lactate is a compound with many uses. It can be used as a solvent, as a starting material for the manufacture of polylactic acid, or as a starting material for numerous other reactions. For example, it can be used as intermediate in lactic acid purification, and as building block in the synthesis of chiral components, e.g., pesticides, and as a starting material for lactide manufacture.

One important use of methyl lactate is use in the manufacture of methyl acrylate, which is a starting material for the manufacture of acrylate polymers. Additionally methyl acrylate is a suitable starting material for acrylic acid and other esters like ethyl acrylate and butyl acrylate.

Methyl lactate can be manufactured from lactic acid, which is obtained through fermentation. In view of the various uses of methyl lactate, there is need in the art for a method for manufacturing methyl lactate, which is efficient and which provides methyl lactate in high yield. The present invention provides such a process.

The present invention pertains to a process for preparing methyl lactate comprising the steps of bringing an aqueous liquid comprising lactic acid, methanol, and at least 5 wt. % of a dissolved chloride salt selected from magnesium chloride, calcium chloride, and zinc chloride to reaction conditions, thereby obtaining methyl lactate, wherein an extractant is provided to the reaction mixture before, during, and/or after formation of methyl lactate, subjecting the reaction mixture to a liquid-liquid separation step wherein an organic phase comprising methyl lactate and extractant is separated from an aqueous phase comprising dissolved chloride salt.

The wt. % is calculated on the weight of the aqueous liquid. It has been found that the process according to the invention makes it possible to manufacture methyl lactate efficiently and in high yield.

More specifically, it has been found that the presence of a dissolved chloride salt selected from magnesium chloride, calcium chloride, and zinc chloride in the reaction mixture results in an increase in reaction rate of the esterification reaction, and product yield as compared to the situation where the specified salt is absent. Further, it has been found that the presence of at least 5 wt. % of these salts improves separation of the methyl lactate and the extractant from the aqueous medium.

It has been found that the process according to the invention also has a number of advantages also as compared to a process wherein in a first step lactic acid is manufactured and separated from a salt solution, and esterification to form methyl lactate takes place in a second step. In the process according to the invention, where the esterification takes place in the presence of the salt, it is not necessary to submit the lactic acid to a purification step. Therewith, the total purification efforts of the lactic acid and the methyl lactate are reduced. Further, as indicated above, the presence of the salt improves the separation process. In consequence, the process according to the invention can be carried out at higher water contents than separation of methyl lactate in the absence of salt, or separation of lactic acid from an aqueous solution. Therewith, less water has to be removed, and this is an economic advantage. Further advantages of the present invention and specific embodiments thereof will become clear from the further specification.

As regards the increase in reaction rate, not wishing to be bound by theory, it is believed that the presence of a dissolved chloride salt selected from magnesium chloride, calcium chloride, and zinc chloride in the reaction mixture leads to a decrease in pH, which results in an increase in reaction rate. It is further believed that the presence of at least 5 wt. % of a dissolved chloride salt selected from magnesium chloride, calcium chloride, and zinc chloride leads to improved phase separation and extraction processes, which methods are particularly suited for separating the esters from the aqueous liquid.

The process according to the invention starts out with an aqueous liquid comprising lactic acid, methanol, and at least 5 wt. % of a dissolved chloride salt selected from magnesium chloride, calcium chloride, and zinc chloride, calculated on the weight of the liquid.

The lactic acid concentration in the aqueous liquid may vary in wide ranges. As a maximum value, a value of 50 wt. % may be mentioned. As a minimum, a value of 1 wt. % may be mentioned. Below that value, economic operation may be difficult. It is preferred for the lactic acid concentration to be in the range of 5-40 wt. %, in particular 10-40 wt. %, more in particular 15-35 wt. %. A range of 20-35 wt. % may be particularly attractive.

The amount of methanol that is present in the aqueous liquid is determined by the amount of lactic acid present in the system. The molar ratio of lactic acid to methanol generally is in the range of 1:1 to 1:10, preferably in the range of 1:1 to 1:5.

In addition to lactic acid and methanol the aqueous liquid comprises at least 5 wt. % of a dissolved chloride salt selected from magnesium chloride, calcium chloride, and zinc chloride, calculated on the weight of the liquid. If the amount of dissolved salt is below 5 wt. % the advantageous effect of the present invention will not be obtained. It may be preferred for the dissolved chloride salt to be present in an amount of at least 10 wt. %, in particular at least 15 wt. %. The maximum for the amount of chloride salt is not critical to the process according to the invention. The maximum will depend on the solubility of the salt in question in the medium. As a general value, a maximum of 40 wt. % may be mentioned. It may be preferred for the aqueous liquid to comprise 10-30 wt. % of dissolved chloride salt, in particular 15 to 25 wt. %. The chloride salt may be selected from magnesium chloride, calcium chloride, and zinc chloride. Mixtures of salts may of course also be applied. The use of magnesium chloride is considered preferred, because it is believed to be particularly effective in ensuring a high separation efficiency, and possibly an increased reaction rate. Additionally, the use of magnesium chloride allows for an attractive integrated process by using a thermal decomposition step. This will be discussed in more detail below.

The aqueous liquid comprising lactic acid, methanol, and chloride salt may be obtained in various manners. In one embodiment, the lactic acid, methanol, and chloride salt are combined in water. However, there are a number of particularly attractive possibilities.

In one embodiment, the aqueous liquid comprising lactic acid, methanol, and chloride salt is obtained by the steps of providing an aqueous liquid comprising a magnesium-, calcium-, or zinc-salt of a lactic acid, acidifying the aqueous liquid by the addition of HCl and adding the methanol before, after, or simultaneous with the addition of HCl. The acidification step results in the conversion of the magnesium-, calcium-, or zinc-lactate into lactic acid, with simultaneous formation of the corresponding chloride salt. By selecting the concentration of lactate salt and HCl, a liquid may be obtained comprising lactic acid and chloride salt in the ranges indicated above.

If so desired the concentration of these components may be increased in various manners, e.g., by adding lactic acid or chloride salt, or by performing a concentration step, wherein water is removed from the system.

The presence of HCl may further increase the reaction rate. Therefore, in one embodiment the reaction mixture comprises additional HCl, e.g., in an amount of 0.5 to 5 wt. %, calculated on the amount of carboxylic acid. While HCl may be added separately to the reaction mixture, in one embodiment of the invention the acidification process is carried out using an excess of HCl as compared to the amount of HCl necessary for neutralisation of the lactate salt. In this embodiment the excess amount of HCl added may, e.g., be in an amount of 0.5 to 5 wt. %, calculated on the amount of HCl added to convert the lactate salt to lactic acid.

The aqueous liquid comprising lactic acid, methanol, and chloride salt is brought to reaction conditions, resulting in the formation of methyl lactate.

Reaction conditions generally include a temperature in the range of 20-150° C., in particular in the range of 30 to 130° C., more in particular in the range of 50 to 100° C.

The pressure during the reaction is not critical, as long as the aqueous liquid remains in the liquid form. Generally, the reaction will be carried out at a pressure of 1-5 bar, preferably under atmospheric conditions.

The step of bringing the aqueous liquid comprising lactic acid, methanol, and chloride salt to reaction conditions, thereby obtaining a methyl lactate ester, can be carried out on the final liquid. It can, however, also be carried out on the liquid during formation, e.g., during an acidification reaction discussed above. In the same way, the separation step discussed below can be carried out after the esterification reaction has been completed, but also during the esterification step, or in some embodiments during the combined acidification/esterification step. Various embodiments are discussed below.

In the process according to the invention, an extraction agent, also indicated as extractant, is provided to the reaction mixture provided before, during, and/or after formation of methyl lactate.

The presence of an extractant results in the formation of a two-phase system which comprises a liquid organic layer comprising the extraction agent and the methyl lactate and an aqueous layer comprising dissolved chloride salt. The system will generally comprise excess methanol, which, dependent on the properties of the extractant, may be present in the water layer and/or the organic layer. Any remaining lactic acid may, dependent on the properties of the extractant, be present in the water layer and/or the organic layer.

The two-phase system can be subjected to a liquid-liquid separation step wherein an organic phase comprising methyl lactate and an extractant is separated from an aqueous solution comprising dissolved chloride salt.

The extractant can be added to the reaction mixture when the formation of methyl lactate has been completed. The extractant can also be added at the start of the reaction, or during the reaction. Combinations are of course also possible. The embodiment wherein extraction agent is provided to the reaction medium before the esterification reaction has the advantage that as soon as any methyl lactate ester is formed, it is transferred to the extractant layer. Since the methyl lactate ester is therewith effectively removed from the reaction mixture, this results in an increased esterification rate.

The extractant should meet the following requirements: It should be able to form a two-phase system and it should not react with lactic acid, methanol, or methyl lactate to a substantive extent (e.g., if at all, less than 2%). The extractant preferably has a boiling point which is such that it can be removed by evaporation, e.g., less than 200° C.

Examples of suitable extractants are aliphatic and aromatic hydrocarbons, such as alkanes and aromatic compounds, ketones, and ethers. Mixtures of various compounds may also be used. It has been found that the selection of a particulate group of extractants is a preferred embodiment of the present invention, because they combine a high reaction rate with a high methyl lactate yield and an efficient separation of methyl lactate from lactic acid, and a high methyl lactate concentration in the extractant, which makes for efficient further processing. It is therefore preferred for the extractant to comprise one or more compounds selected from the group of C5+ ketones, C3-C10 ethers, and C6-C10 aromatic compounds.

In one embodiment, the extractant comprises C5+ ketones, wherein C5+ stands for ketones with at least 5 carbon atoms. The use of C9+ ketones is less preferred, because the solubity of methyl lactate in this type of compounds is limited. The use of C5-C8 ketones is therefore preferred. The use of methyl-isobutyl-ketone (MIBK) has been found to be particularly attractive.

Examples of suitable C3-C10 ethers are C3-C6 ethers, e.g., methyl tert-butyl ether (MTBE) and diethyl ether (DEE).

Examples of suitable C6-C10 aromatic compounds include toluene, xylene, and ethylbenzene.

An extractant comprising one or more compounds selected from C5+ ketones and C3-C10 ethers, in particular C5-C8 ketones, is considered particularly preferred, because the use of these compounds has been found to yield an efficient process because an extractant with a high methyl lactate concentration can be obtained. To obtain the benefits of the selection of the indicated compounds it is preferred for the extractant to comprise at least 50 wt. % of the compounds mentioned above as suitable or preferred extractants, in particular at least 80 wt. %, more in particular at least 90 wt. %.

The amount of extractant used in the present invention is generally not critical. The minimum amount will be determined by the amount necessary to ensure an effective separation process. The maximum amount will be determined by commercial operation, where the addition of further extractant does not lead to an improved separation, but only leads to increased reactor volume. As a general range, a volume ratio of (water+lactic acid+methanol++ salt+methyl lactate): extractant within the range of 1:0.01 to 1:10, in particular 1:0.1 to 1:10 may be mentioned.

It is preferred for at least 80% of the methyl lactate present in the system to be present in the liquid organic layer, in particular at least 90%, more in particular at least 95%, still more in particular at least 98%. The liquid organic layer typically comprises less than 20 wt. % of water, more in particular less than 10 wt. % of water, still more in particular less than 5 wt. % of water.

Efficient separation between the ester in the organic phase and the aqueous phase can e.g. be obtained by performing multistage countercurrent operation.

The aqueous layer comprises dissolved chloride salt as described above, and preferably less than 5 wt. % of methyl lactate, more preferably less than 2 wt. % of methyl lactate, and even more preferably less than 1 wt. % of methyl lactate.

The aqueous layer preferably contains less than 5 wt. % of the total amount of lactic acid provided to the system, more preferably less than 2 wt. %, still more preferably less than 1 wt. %.

The process according to the invention preferably shows a conversion of at least 90%, expressed as the amount of lactic acid converted, calculated on the amount of lactic acid originally provided to the system. More preferably the conversion is at least 95%, still more preferably at least 99%.

The process according to the invention can be operated to a yield of at least 90%, expressed as the amount of methyl lactate ester resulting from the process calculated on the theoretical yield, calculated from the amount of lactic acid originally provided to the system. Preferably the yield is at least 95%, more preferably at least 98%, still more preferably at least 99%. It has been found that the process according to the invention can give such high yields, especially when it is ensured that proper recycling steps are incorporated into the process design, e.g., in combination with the use of a multistage countercurrent process.

As indicated above, the presence of dissolved chloride salt during the esterification reaction leads to an increase in reaction rate. It was further found that the presence of dissolved chloride salt enhances separation of the methyl lactate ester by extraction. More specifically, an increase in the concentration of dissolved chloride salt may lead to a higher distribution coefficient of the methyl lactate between the organic layer and the aqueous layer, resulting in an improved methyl lactate yield in the organic layer and a lower organic content of the aqueous layer. It is therefore preferred for the chloride salt solution to have a relatively high concentration. In this embodiment it may be preferred for the chloride salt concentration in the aqueous liquid to be at least 10 wt. %, more preferably at least 15 wt. %, even more preferably at least 20 wt. %.

The step of performing a liquid-liquid separation wherein an organic phase comprising methyl lactate and an extractant is separated from an aqueous solution comprising dissolved chloride salt can be carried out by methods known in the art for liquid-liquid separation. Examples of suitable apparatus and methods for liquid-liquid separation include decantation, settling, centrifugation, use of plate separators, use of coalescers, and use of hydrocyclones. Combination of different methods and apparatus may also be used.

The method of the invention may further comprise a water removal step prior to or during esterification. For example, water may be removed before adding the methanol, but after adding the hydrogen chloride. Such a step may allow for a higher concentration of chloride salt and/or a higher concentration of lactic acid. This may increase the esterification reaction rate and/or increase the amount of methyl lactate in the extractant. Preferred lactic acid concentrations to which can be concentrated are mentioned above for the aqueous mixture. An upper limit may be derived from the solubility of chloride salt in the solution, as the presence of precipitated salt does not provide additional advantages, but may result in processing issues.

As indicated above, it is preferred for the chloride salt used in the present invention to be magnesium chloride. One reason why this salt is preferred is that it allows an attractive method of processing for the chloride salt solution, namely by thermal decomposition. Therefore, in one embodiment of the present invention, the magnesium chloride solution resulting from the separation step is provided to a thermal decomposition step, where it is converted into magnesium oxide and hydrogen chloride. The process of thermal decomposition is also known under the terms thermal hydrolysis and thermohydrolysis.

Thermal decomposition is generally conducted at a temperature of a least 300° C. Preferably, thermal decomposition is conducted at a temperature of at least 350° C. Due to energy costs, the temperature is preferably below 1000° C., more preferably below 800° C. For example, the temperature at which thermal decomposition is conducted may be 350-600 or 400-450° C.

Preferably, the magnesium chloride solution has a magnesium chloride concentration of 15-40 wt. %, more preferably 25-35 wt. %. Too high amounts of magnesium chloride present in the solution may result in precipitation of magnesium chloride upon entering the thermohydrolysis unit. Water may be added to or removed from the hydrogen chloride solution recovered in the method of the invention in order to obtain a desirable magnesium chloride concentration.

Suitable apparatuses for conducting thermal decomposition are known in the art. For example, a spray roaster or a fluid bed roaster can be used. Such apparatuses can for example be obtained at SMS Siemag, Andritz. Tenova, CMI, and Chemline. The magnesium oxide obtained in thermal decomposition will be in solid form. It can, if so desired, be recycled for use in a fermentation process, in particular as a neutralizing agent. The MgO can be used directly, but it is also possible to convert it to magnesium hydroxide by reaction with water. The hydrogen chloride obtained in the thermal decomposition may, if so desired, be used in an acidification step.

In one embodiment, the invention pertains to an integrated process encompassing all steps from manufacturing lactic acid through a fermentation step until the formation of the methyl lactate ester. This makes for efficient integration of various steps and a high methyl lactate yield.

If so desired, a step for converting methyl lactate into methyl acrylate can also be provided.

Therefore, in one embodiment, the method according to the invention further comprises a fermentation step, wherein an aqueous feed comprising a lactic acid salt is formed. Such a step typically comprises the substeps of fermenting a carbon source by means of a micro-organism to form a fermentation medium comprising lactic acid, and (partially) neutralizing the fermentation medium in order to establish a desirable pH by adding a neutralizing agent, in this case preferably a calcium base, a zinc base, or a magnesium base, more in particular a magnesium base, to form the corresponding lactate salt. Subsequently, biomass may, if so desired, be separated from the fermentation medium, for example by (ultra)filtration, centrifugation or decantation of the biomass. It has been found in general that biomass removal leads to an end product with better properties, including a lower contaminant content. The lower contaminant content also leads to a better product color, as contaminants often result in the formation of color compounds which are difficult to remove. Therefore, it is preferred to effect a biomass removal step. This is the more so since the presence of biomass may also impact so-called crud formation, which leads to product losses and hampers liquid/liquid separation.

As described above, magnesium oxide obtained in the thermal decomposition step can be recycled in the precipitation step as a neutralizing agent or precursor thereof.

In one embodiment the process according to the invention further comprises a step wherein the methyl lactate is subjected to a dehydration reaction in the presence of a catalyst to form methyl acrylate. The process is suitably carried out in the gas phase. The reaction temperature is, e.g., 300-500° C. Reaction pressure is, e.g., in the range of 0.5-3 bar, and suitably atmospheric. An inert gas may be added to reduce the partial pressure by dilution. Suitable catalysts include dehydrogenation catalysts known in the art. Examples include catalysts based on calcium sulphate, calcium phosphate, calcium pyrophosphate, and combinations thereof. Suitable promotors include sodium sulphate, copper sulphate, manganese sulphate, iron sulphate, magnesium sulphate, aluminium sulphate, sodium nitrate, sodium phosphate, and potassium phosphate.

FIG. 1 illustrates the process according to the invention embedded in an integrated process. A fermentation process is carried out in fermentation reactor (1) generating lactic acid. A base is added during fermentation (not shown), resulting in the formation of a lactate salt. The base preferably is a calcium base, e.g. calcium oxide, hydroxide, or carbonate, a magnesium base, e.g., magnesium oxide, hydroxide or carbonate, or a zinc base, e.g., zinc oxide, hydroxide, or carbonate. The use of a magnesium base is preferred. A product stream (2) comprising a lactate salt, preferably calcium lactate, magnesium lactate, or zinc lactate, in particular magnesium lactate, is withdrawn from the fermentation reactor, and provided to an acidification/esterification reactor. If so desired, intermediate purification steps such as biomass removal may be carried out in manners known in the art. In acidification/esterification reactor (3), methanol is added through line (14), and hydrogen chloride is added through line (9). The hydrogen chloride may be in the gas phase or in solution in water. The hydrogen chloride may be added prior to the addition of methanol, simultaneous with the addition of methanol, or after the addition of methanol. An extractant is provided through line (16). The reactor is brought to esterification conditions. Next, a separation step is carried out. In the figure, this is presented as a separate step (5), but it may be carried out in the esterification reactor. The separation step encompasses the a liquid-liquid separation step, yielding an aqueous stream (6), which comprises the chloride salt and an organic phase, which comprises extractant and methyl lactate. If the chloride salt is magnesium chloride, stream (6) can be provided to a thermal decomposition step (7), where the aqueous magnesium chloride solution is decomposed to form magnesium oxide, removed through line (8), and hydrogen chloride, removed through line (9). The hydrogen chloride may be recycled to the acidification step as illustrated in the figure, either as gas, or after having been absorbed in an aqueous liquid to form a solution. The magnesium oxide may be recycled to the fermentation step (1) (via lines not shown), either directly or after conversion into magnesium hydroxide or carbonate. The product stream (10) removed from the separation step (5) comprises methyl lactate in extractant. It will generally also comprise methanol, as the esterification reaction is generally carried out in the presence of a surplus of methanol. The product stream (10) may be provided to a separation step (11), where the methanol and extractant are separated from the methyl lacate ester. The separation step yields a product stream (12) comprising the methyl lactate ester, a methanol stream (13), which can be provided to the methanol feed (14), and an extractant recycle stream (16). There may be a bottom stream (15) which may contain lactic acid and optional condensation products. This stream, if present, may be recycled to the esterification step, or otherwise disposed of.

Figure 2:
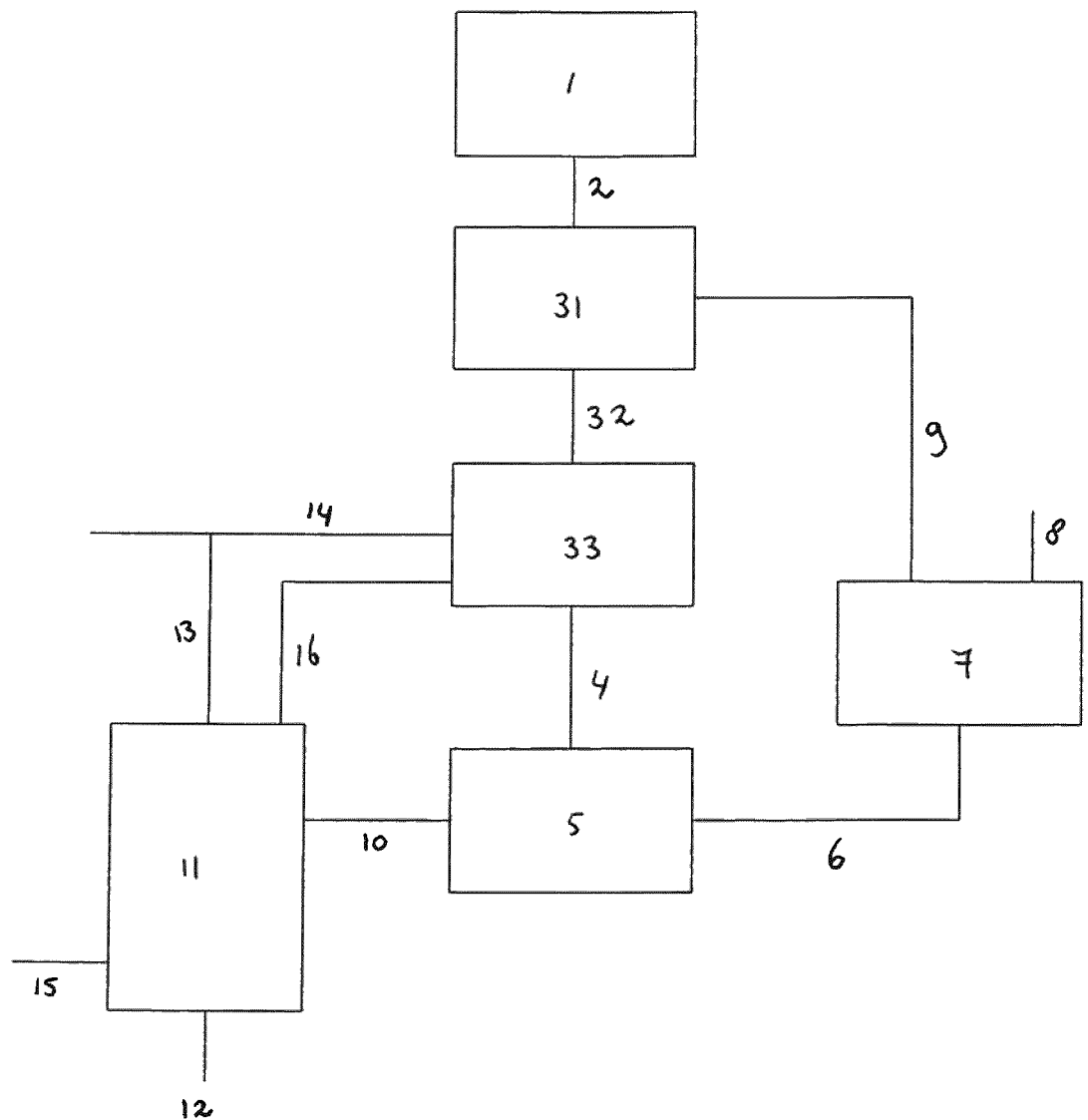

FIG. 2 provides a variation on the process of FIG. 1. In the process of FIG. 2 the acidification step and the esterification step are separated, with the acidification step being carried out in acidification reactor (31), to which hydrochloric acid is provided through line (9). The acidified product, which is an aqueous liquid comprising methyl lactate ester and chloride salt is provided through line (32) to esterification reactor (33) to which methanol is provided through line (14).

In one embodiment of the present invention, the esterification step and the liquid-liquid separation step are combined in a single step in a single reactor. In one embodiment, this reactor is operated in countercurrent operation, wherein the lactic acid is provided to the top of the reactor in a solution comprising a chloride salt as described above. Methanol and extractant are provided to the bottom of the reactor, in the same or in separate streams. The methyl lactate ester and the extractant are withdrawn from the top of the reactor. An aqueous solution comprising the dissolved chloride salt is withdrawn from the bottom of the reactor. It has been found that this embodiment allows obtaining a high conversion in combination with a high yield, as described above. This embodiment is illustrated in FIG. 3, without being limited thereto or thereby.

Figure 3:
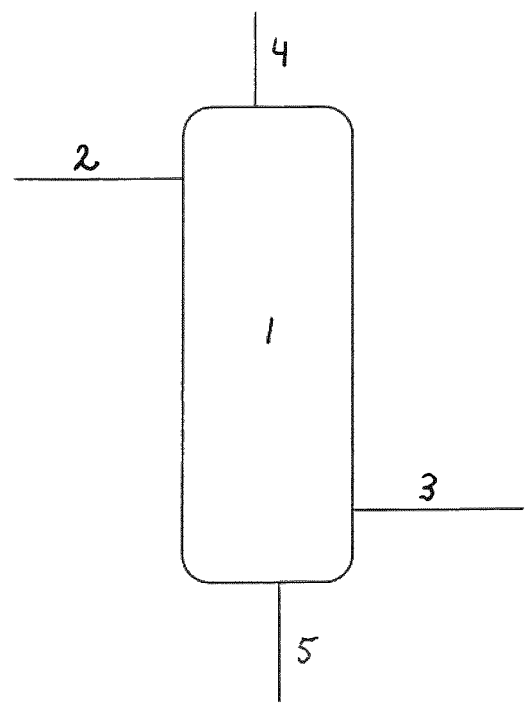

FIG. 3 shows a reactor (1) provided with an inlet (2) at the top, wherein an aqueous liquid, e.g., a solution comprising lactic acid and soluble chloride salt is provided to the reactor. Methanol and extractant are provided to the bottom of the reactor through line 3. The reactor is at esterification conditions discussed above. A top stream is withdrawn from the reactor through line (4). The top stream comprises methyl lactate and extractant. A bottom stream comprising the chloride salt is withdrawn through line (5). For information on the components in the various liquids, processing conditions, and processing of the resulting products reference is made to the general description above.

It will be evident to the skilled person that the various aspects of the present invention which are described above in different paragraphs may be combined.

While the figures illustrate various integrated processes, it is within the scope of the skilled person to combine the various elements of the process in suitable manners.

The invention and certain embodiments of the inventions are illustrated by the following examples and/or embodiments, without being limited thereto or thereby.

EXAMPLE 1

General Procedure

Reaction vessels were charged with lactic acid, water, and optionally MgCl2 and/or extractant. The mixture was heated to 60° C. Where necessary, i.e., for hexane and methyl-tert. butyl ether, the reaction was carried out in an autoclave, to prevent evaporation of the extractant. The other experiments were carried out in glass vessels.

Table 1 below provides the compositions tested:

TABLE 1

| Exp. No. | MgCl$_2$ | Extractant |
|---|---|---|
| Comparative A | – | — |
| Comparative B | + | — |
| Comparative C | – | methyl-isobutyl ketone (MIBK) (4-methyl-2-pentanone) |
| Example 1 | + | methyl-isobutyl ketone (MIBK) (4-methyl-2-pentanone) |
| Example 2 | + | methyl-ethyl ketone (MEK) (2-butanone) |

TABLE 1-continued

| Exp. No. | MgCl$_2$ | Extractant |
|---|---|---|
| Example 3 | + | Toluene |
| Example 4 | + | Hexane |
| Example 5 | + | methyl-tert butyl ether (MTBE) |

For all experiments, the molar ratio of lactic acid to methanol is 1:3. The molar ratio of lactic acid to magnesium chloride (if used) is 1:2. The volume ratio of the organic phase and the aqueous phase at the start of the reaction is 1:1. Reaction time is 24 hours, except for examples 4 and 5, which were carried out in an autoclave for a period of 7 hours. In all experiments the initial concentration of lactic acid in the aqueous medium (without methanol and extractant) was 25 wt. %.

At t=0 methanol was added. After methanol addition the temperature recovered to 60° C. within a few minutes. Magnetic stirring was applied at such a rate that in case of a two-phase system a finely divided emulsion was formed, to prevent mixing to be a limiting factor.

At specific times samples were taken for analysis. The mixture was allowed to settle in case of a two-phase system. Then four drops (about 0.05 ml) of the mixture or upper layer were diluted in 1.5 ml of butanol as solvent.

Results of Kinetic Experiments

Figure 4:
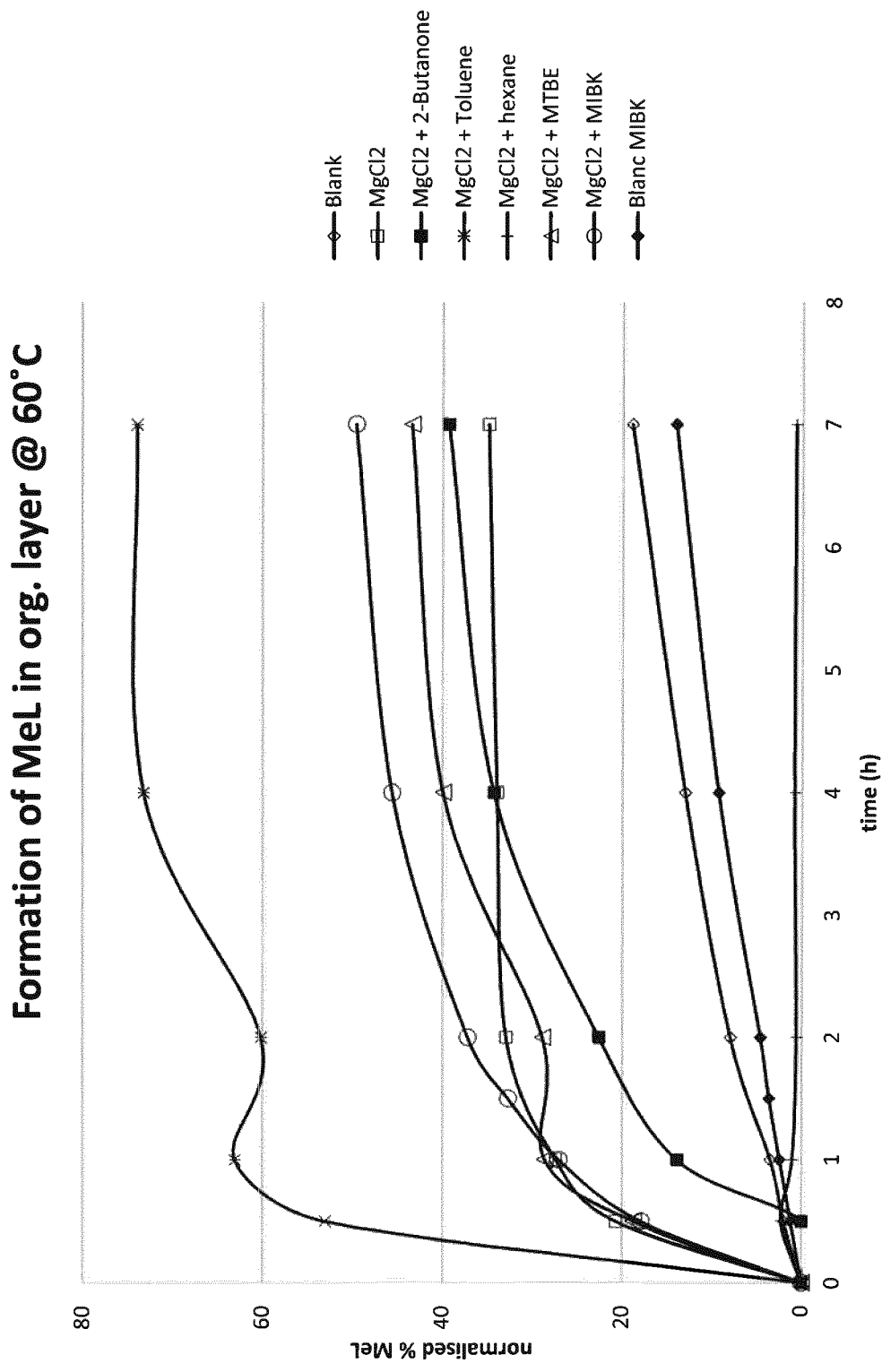

Samples were analysed by GLC (area). No response factors were applied, so the results are semi-quantitative. The GC-areas of MeL and MeOH were added and normalised on 100%. T The results are presented in FIG. 4. FIG. 4 shows the formation of methyl lactate in the organic layer at 60° C., expressed as the amount of methyl lactate in the organic layer, calculated on the total of methyl lactate and methanol in the organic layer (MeOH+MeL=100%).

From FIG. 4, the following conclusions may be drawn.

The addition of magnesium chloride results in an increased ration rate (compare MgCl2 (Comparative B) with Blanc (Comparative A)). However, these systems do not give phase separation in the absence of extractant.

The use of MIBK in the absence of MgCl2 does not seem to influence the reaction rate (compare Blanc MIBK (Comparative C) with Blanc (Comparative A)).

The use of the combination of MgCl2 and 2-butanon, toluene, MTBE, and MIBK (Examples 1, 2, 3, and 5) all result in the presence of methyl lactate in the organic layer. [Note that as the data are expressed calculated on the amount of methyl lactate+methanol, so no conclusions can be drawn about the absolute amount of methyl lactate.]

For hexane (Example 6), there was either no methyl lactate or a very large amount of methanol in the organic phase. Hexane may be a less suitable extractant.

Analysis of Organic and Aqueous Layers

For Examples 1 and 3, the composition of the organic and aqueous layers after 24 hours were analysed in more detail. The results are presented in Table 2.

TABLE 2

| | | GC (w %) | | | Free acid (w % as HL) | Water (w %) |
|---|---|---|---|---|---|---|
| Exp. | Layer | MeOH | MeL | MeLL* | | |
| 1 (MIBK) | Organic | 4.0 | 7.4 | <0.1 | 3.2 | 3.8 |
| 1 (MIBK) | Aqueous | 13 | 5.5 | <0.1 | 4.8 | |
| 3 (Toluene) | Organic | <0.1 | 2.8 | <0.1 | 0.053 | 0.096 |
| 3 (Toluene) | Aqueous | 16 | 11 | 0.1 | 11 | |

*MeLL = methyl lactoyl lactate

From the table it can be seen that toluene in Example 3 is a selective extractant for methyl lactate as compared to methanol and lactic acid and water. The toluene layer contains only methyl lactate. On the other hand, in the experiment, a relatively large amount of methyl lactate remained in the aqueous phase. This means that for complete extraction of the methyl lactate large volumes of toluene will be required. This can, e.g., be addressed via a multiple step extraction.

It can be seen that when using MIBK as extractant, larger concentrations in the organic phase are obtained, which means that less extractant will be required to extract the methyl lactate. On the other hand, the organic layer contains higher amounts of lactic acid and methanol, showing that extraction is less selective.

The invention claimed is:

1. Process for preparing methyl lactate comprising the steps of
   providing an aqueous liquid comprising lactic acid, methanol, and at least 5 wt. % of a dissolved chloride salt selected from magnesium chloride, calcium chloride, and zinc chloride,
   subjecting the aqueous liquid to an esterification step by bringing the aqueous liquid to reaction conditions, thereby obtaining methyl lactate, wherein
      an extractant is provided to the reaction mixture before, during, and/or after formation of methyl lactate, and
      the extractant is selected from the group of C5+ ketones, C3-C10 ethers, and C6-C10 aromatic compounds,
   subjecting the reaction mixture to a liquid-liquid separation step wherein an organic phase comprising methyl lactate and extractant is separated from an aqueous phase comprising dissolved chloride salt.

2. Process according to claim 1, wherein the dissolved chloride salt is magnesium chloride.

3. Process according to claim 1, wherein the dissolved chloride salt is present in an amount of at least 10 wt. %.

4. Process according to claim 3, wherein the dissolved chloride salt is present in an amount of at least 15 wt. %.

5. Process according to claim 1, wherein extractant is provided to the reaction medium before formation of methyl lactate.

6. Process according to claim 1, wherein the extractant is one or more compounds selected from C5+ ketones and C3-C10 ethers.

7. Process according to claim 6, wherein the extractant is one or more compounds selected from C5-C8 ketones.

8. Process according to claim 7, wherein the extractant is methyl isobutyl ketone.

9. Process according to claim 1 which further comprises preparing the aqueous liquid comprising lactic acid, methanol, and dissolved chloride salt by the steps of
   providing an aqueous liquid comprising a calcium, magnesium, or zinc salt of lactic acid, subjecting the aqueous liquid to an acidification step by the addition of HCl, and adding the methanol before, after, or simultaneous with the addition of HCl.

10. Process according to claim 9, wherein the acidification step is combined with the esterification step, and optionally the separation step.

11. Process according to claim 9, which additionally comprises a fermentation step wherein a carbon source is fermented by means of a micro-organism in a fermentation broth to form lactic acid and neutralizing at least part of the lactic acid by adding a base selected from an oxide, hydroxide, or carbonate of zinc, magnesium, or calcium, thereby obtaining a zinc-, magnesium-, or calcium carboxylate.

12. Process according to claim 1, wherein the dissolved salt is magnesium chloride and the process comprises the additional step of subjecting a solution of magnesium chloride to a thermal decomposition step at a temperature of at least 300° C., thereby decomposing magnesium chloride into magnesium oxide and hydrogen chloride.

13. Process according to claim 12 wherein the hydrogen chloride obtained by the thermal decomposition step is provided in an acidification step to the aqueous liquid comprising a calcium, magnesium, or zinc salt of lactic acid and/or wherein the magnesium oxide is provided as neutralising agent to a fermentation step, either directly or after conversion into an oxide, hydroxide, or carbonate.

14. Process according to claim 1 which further comprises a step wherein methyl lactate is subjected to a dehydration reaction in the presence of a catalyst to form methyl acrylate.

15. Process according to claim 1, wherein the lactic acid is present in an amount in the range of 5-40 wt. %.

16. Process according to claim 15, wherein a molar ratio of the lactic acid to the methanol is in the range of 1:1 to 1:10.

17. Process according to claim 1, wherein the dissolved chloride salt is present in an amount in the range of from 15-25 wt. %.

18. Process for preparing methyl lactate comprising the steps of
providing an aqueous liquid comprising lactic acid, methanol, and at least 5 wt. % of a dissolved chloride salt selected from magnesium chloride, calcium chloride, and zinc chloride,
subjecting the aqueous liquid to an esterification step by bringing the aqueous liquid to reaction conditions, thereby obtaining methyl lactate, wherein an extractant is provided to the reaction mixture before, during, and/or after formation of methyl lactate, and
subjecting the reaction mixture to a liquid-liquid separation step wherein an organic phase comprising methyl lactate and extractant is separated from an aqueous phase comprising dissolved chloride salt; wherein the esterification step and the liquid-liquid separation step are combined in a single step in a single reactor which is operated in countercurrent operation, wherein the lactic acid is provided to the top of the reactor in a solution comprising a chloride salt, methanol is provided to the bottom of the reactor, methyl lactate is withdrawn from the top of the reactor, and an aqueous solution comprising the dissolved chloride salt is withdrawn from the bottom of the reactor.

19. Process according to claim 18, wherein the extractant is selected from the group of C5+ ketones, C3-C10 ethers, and C6-C10 aromatic compounds.

20. Process for preparing methyl lactate comprising the steps of
providing an aqueous liquid comprising lactic acid, methanol, and at least 5 wt. % of a dissolved magnesium chloride salt,
subjecting the aqueous liquid to an esterification step by bringing the aqueous liquid to reaction conditions, thereby obtaining methyl lactate, wherein
an extractant is provided to the reaction mixture before, during, and/or after formation of methyl lactate, and
the extractant is one or more compounds selected from C5-C8 ketones,
subjecting the reaction mixture to a liquid-liquid separation step wherein an organic phase comprising methyl lactate and extractant is separated from an aqueous phase comprising dissolved magnesium chloride salt.

* * * * *